US008046050B2

(12) United States Patent
Govari et al.

(10) Patent No.: US 8,046,050 B2
(45) Date of Patent: Oct. 25, 2011

(54) POSITION SENSING SYSTEM FOR ORTHOPEDIC APPLICATIONS

(75) Inventors: Assaf Govari, Haifa (IL); Avi Shalgi, Tel-Aviv (IL); Susel Pesach, Haifa (IL); David Reznick, Shimshit (IL)

(73) Assignee: Biosense Webster, Inc., Diamond Bar, CA (US)

( * ) Notice: Subject to any disclaimer, the term of this patent is extended or adjusted under 35 U.S.C. 154(b) by 1461 days.

(21) Appl. No.: 11/062,258

(22) Filed: Feb. 18, 2005

(65) Prior Publication Data
US 2005/0245821 A1 Nov. 3, 2005

Related U.S. Application Data

(60) Provisional application No. 60/550,924, filed on Mar. 5, 2004.

(51) Int. Cl.
*A61B 5/05* (2006.01)
*G01C 9/00* (2006.01)
(52) U.S. Cl. .......................................... 600/424; 702/150
(58) Field of Classification Search .................. 600/407, 600/414, 417, 424, 426, 429; 128/899; 606/130
See application file for complete search history.

(56) References Cited

U.S. PATENT DOCUMENTS

| | | | |
|---|---|---|---|
| 5,042,486 A * | 8/1991 | Pfeiler et al. .................. 600/424 |
| 5,211,165 A | 5/1993 | Dumoulin et al. | |
| 5,389,101 A * | 2/1995 | Heilbrun et al. ............. 606/130 |
| 5,391,199 A | 2/1995 | Ben-Haim | |
| 5,437,277 A | 8/1995 | Dumoulin et al. | |
| 5,443,489 A | 8/1995 | Ben-Haim | |
| 5,558,091 A | 9/1996 | Acker et al. | |
| 5,592,939 A * | 1/1997 | Martinelli ..................... 600/424 |
| 5,603,318 A * | 2/1997 | Heilbrun et al. ............. 600/426 |
| 5,729,129 A * | 3/1998 | Acker ....................... 324/207.12 |
| 5,769,861 A * | 6/1998 | Vilsmeier ..................... 606/130 |
| 5,891,034 A * | 4/1999 | Bucholz ....................... 600/426 |
| 5,980,535 A * | 11/1999 | Barnett et al. ................ 606/130 |
| 5,999,837 A * | 12/1999 | Messner et al. .............. 600/407 |
| 6,147,480 A | 11/2000 | Osadchy et al. | |

(Continued)

FOREIGN PATENT DOCUMENTS

EP 1005835 6/2000

(Continued)

OTHER PUBLICATIONS

Biosense Webster, Inc., U.S. Appl. No. 10/632,217—pending.

(Continued)

*Primary Examiner* — Long V. Le
*Assistant Examiner* — Angela M Hoffa
(74) *Attorney, Agent, or Firm* — Louis J. Capezzuto

(57) ABSTRACT

A surgical tracking system includes a wireless position sensor, which is adapted to be implanted in a bone of a subject, and responsively to externally-applied magnetic fields within a working volume of the tracking system, to generate and transmit sensor signals indicative of coordinates of the position sensor within the bone. A plurality of field generator coils are adapted to generate the magnetic fields so as to define the working volume. The field generators are fixed in predetermined locations to a reference structure, which is movable relative to the subject in order to position the working volume so as to intercept the bone. A system controller is coupled to receive and process the sensor signals so as to determine the coordinates of the position sensor within the bone.

39 Claims, 13 Drawing Sheets

U.S. PATENT DOCUMENTS

| | | | |
|---|---|---|---|
| 6,239,724 B1 | 5/2001 | Doron et al. | |
| 6,314,310 B1 | 11/2001 | Ben-Haim et al. | |
| 6,332,089 B1 | 12/2001 | Acker | |
| 6,366,799 B1 * | 4/2002 | Acker et al. | 600/424 |
| 6,373,240 B1 | 4/2002 | Govari | |
| 6,402,762 B2 * | 6/2002 | Hunter et al. | 606/130 |
| 6,427,314 B1 | 8/2002 | Acker | |
| 6,484,118 B1 * | 11/2002 | Govari | 702/150 |
| 6,499,488 B1 * | 12/2002 | Hunter et al. | 128/899 |
| 6,618,612 B1 | 9/2003 | Acker | |
| 6,687,531 B1 * | 2/2004 | Ferre et al. | 600/424 |
| 6,690,963 B2 | 2/2004 | Ben-Haim et al. | |
| 6,694,167 B1 * | 2/2004 | Ferre et al. | 600/424 |
| 6,738,656 B1 * | 5/2004 | Ferre et al. | 600/426 |
| 6,892,090 B2 * | 5/2005 | Verard et al. | 600/424 |
| 6,934,575 B2 * | 8/2005 | Ferre et al. | 600/427 |
| 7,010,369 B2 * | 3/2006 | Borders et al. | 700/90 |
| 7,152,608 B2 * | 12/2006 | Hunter et al. | 128/899 |
| 7,313,430 B2 * | 12/2007 | Urquhart et al. | 600/429 |
| 2002/0052604 A1 | 5/2002 | Simon et al. | |
| 2002/0065455 A1 | 5/2002 | Ben-Haim et al. | |
| 2002/0193685 A1 * | 12/2002 | Mate et al. | 600/424 |
| 2003/0120150 A1 * | 6/2003 | Govari | 600/424 |
| 2003/0192557 A1 | 10/2003 | Krag | |
| 2003/0216639 A1 | 11/2003 | Gilboa et al. | |
| 2004/0239314 A1 | 12/2004 | Govani | |

FOREIGN PATENT DOCUMENTS

| | | |
|---|---|---|
| EP | 1321097 A | 6/2003 |
| EP | 1382308 A | 1/2004 |
| WO | WO 96/57698 A1 | 2/1996 |
| WO | 9729683 A | 8/1997 |

OTHER PUBLICATIONS

Biosense Webster, Inc., U.S. Appl. No. 10/706,298—pending.

Biosense Webster, Inc., U.S. Appl. No. 10/754,751—pending.

* cited by examiner

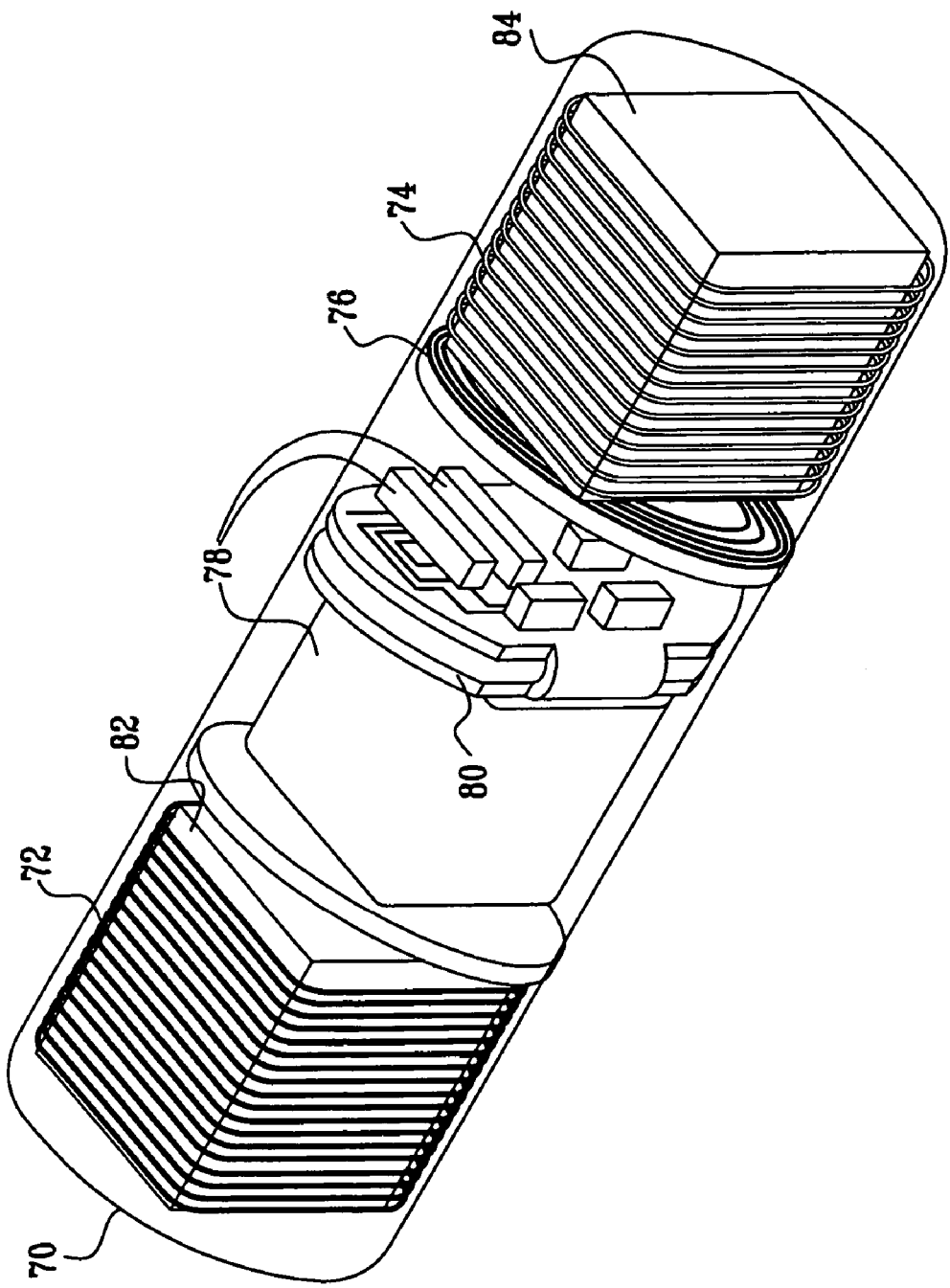

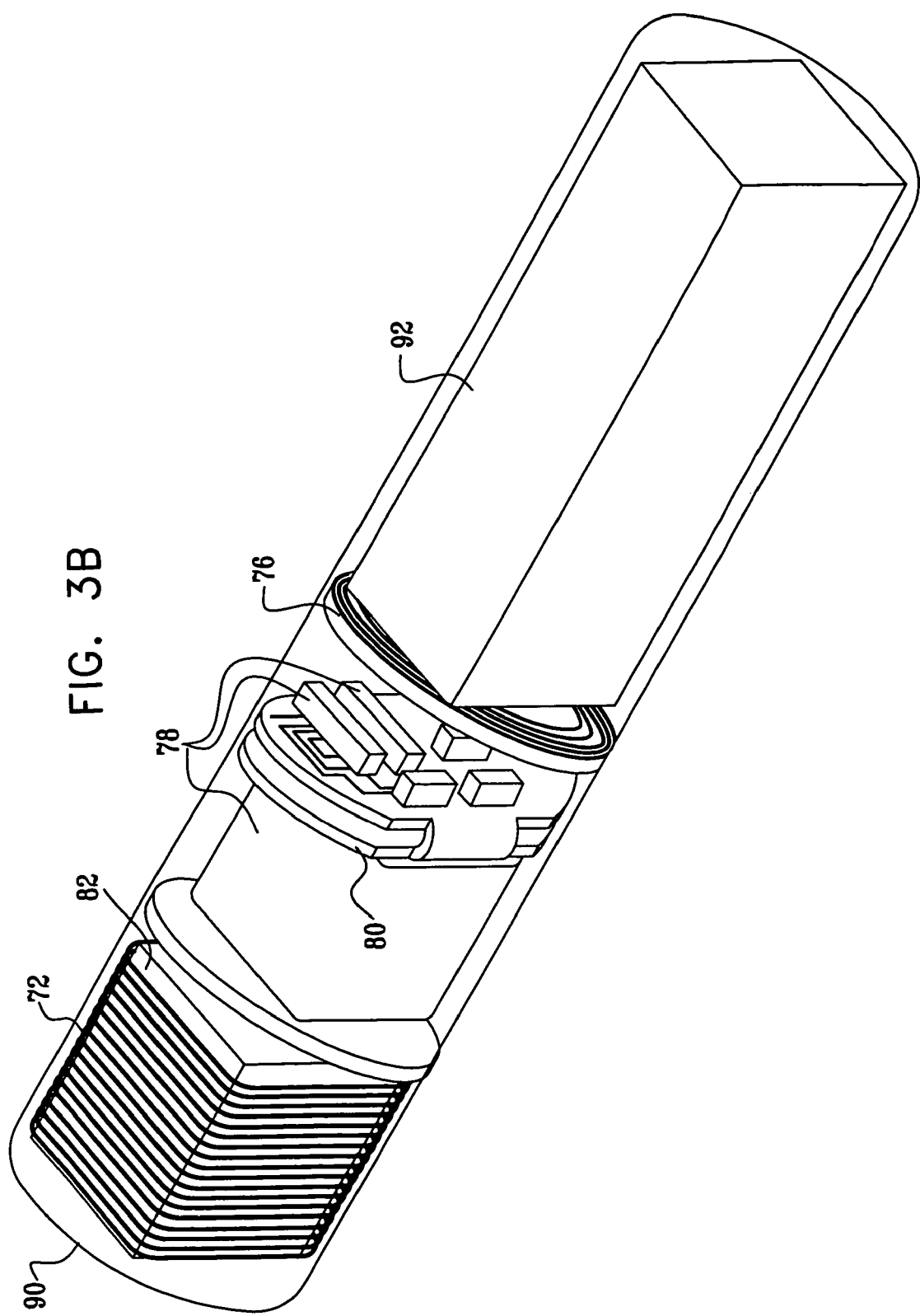

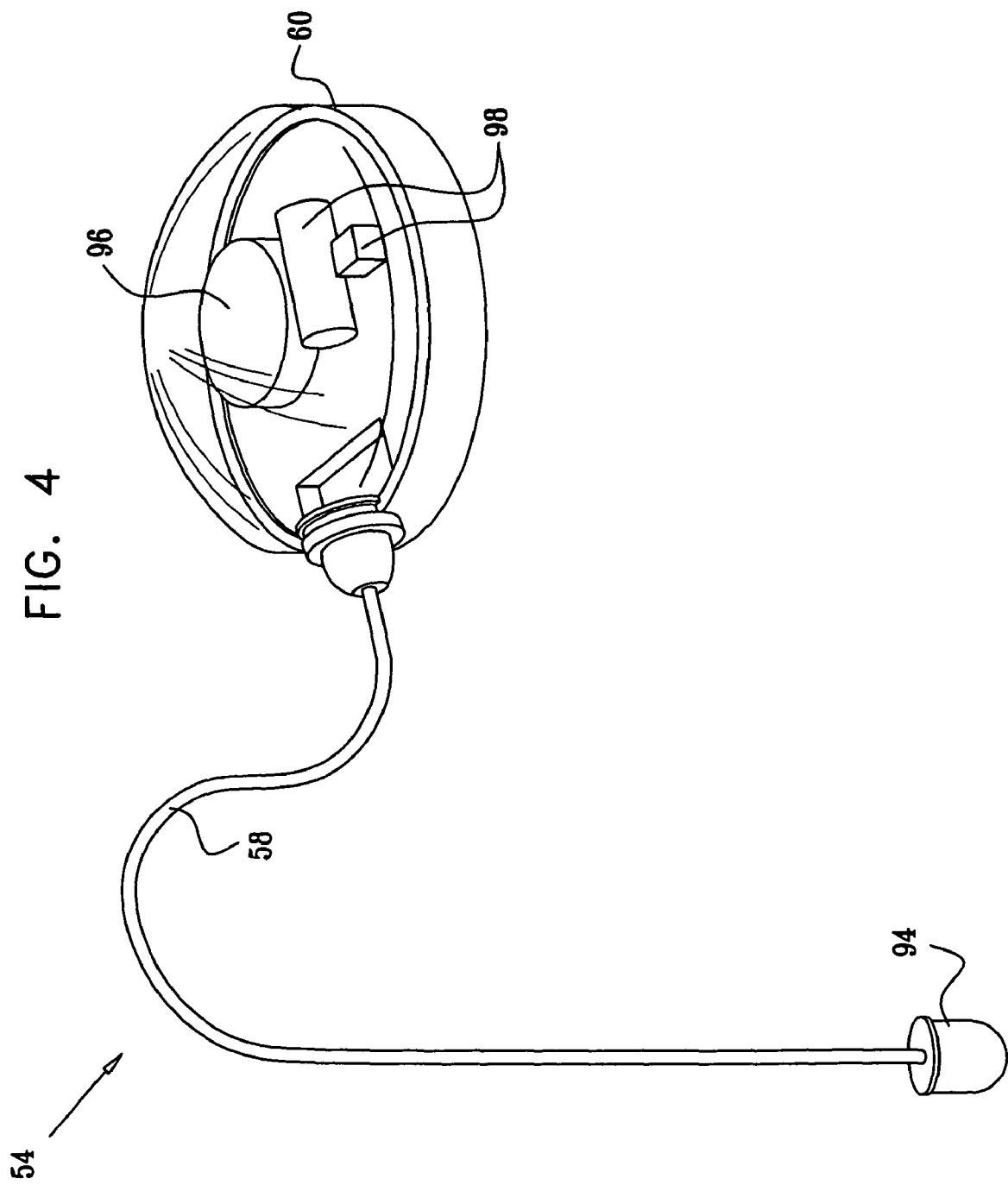

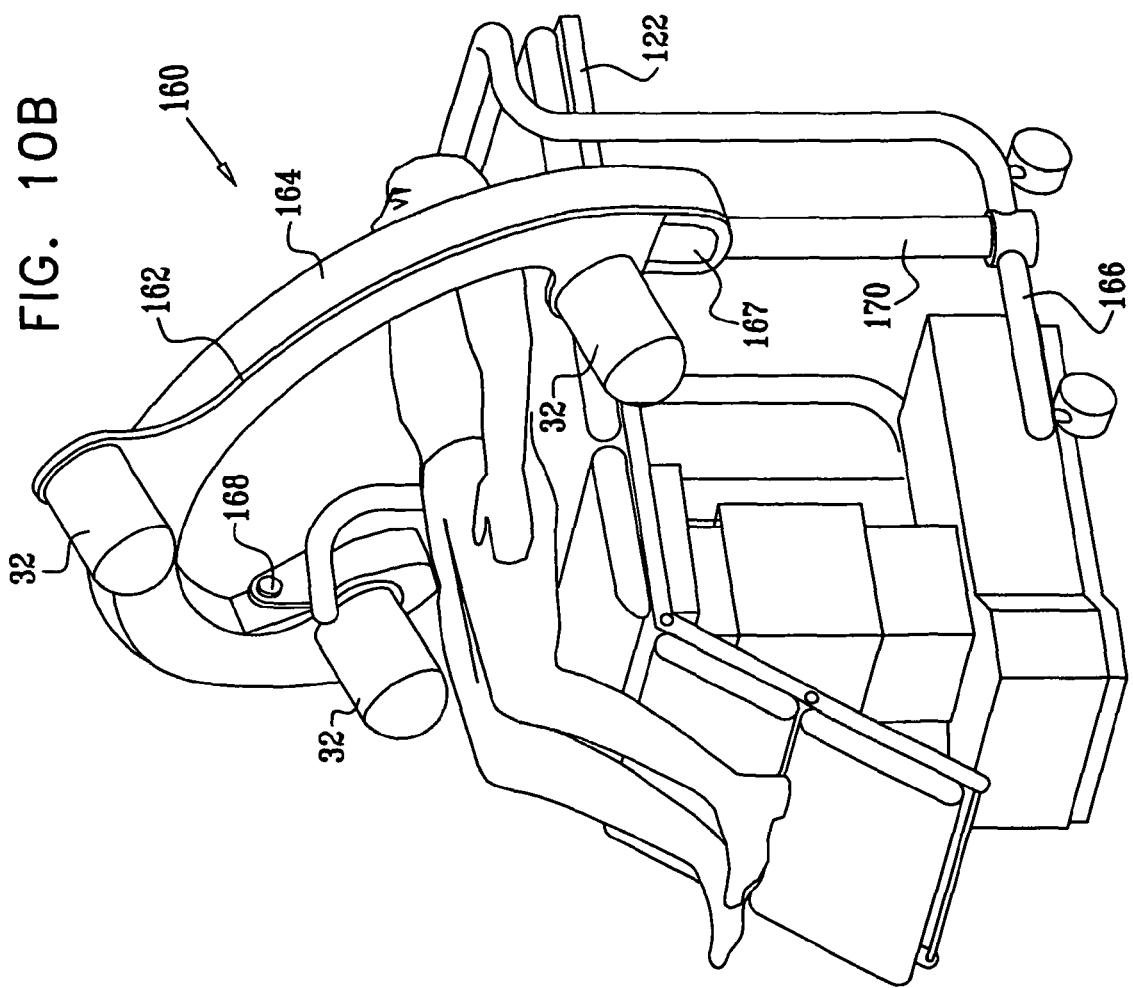

POSITION SENSING SYSTEM FOR ORTHOPEDIC APPLICATIONS

This claims the benefit of U.S. Provisional Application No. 60/550,924 filed on Mar. 5, 2004.

FIELD OF THE INVENTION

The present invention relates generally to intrabody tracking systems, and specifically to wireless methods and devices for tracking the position and orientation of an object in the body.

BACKGROUND OF THE INVENTION

Various methods and systems are known in the art for tracking the position of a medical probe or implant inside the body of a subject.

For example, U.S. Pat. Nos. 5,391,199 and 5,443,489 to Ben-Haim, whose disclosures are incorporated herein by reference, describe systems wherein the coordinates of an intrabody probe are determined using one or more field sensors, such as a Hall effect device, coils, or other antennae carried on the probe. Such systems are used for generating three-dimensional location information regarding a medical probe or catheter. Preferably, a sensor coil is placed in the catheter and generates signals in response to externally-applied magnetic fields. The magnetic fields are generated by three radiator coils, fixed to an external reference frame in known, mutually-spaced locations. The amplitudes of the signals generated in response to each of the radiator coil fields are detected and used to compute the location of the sensor coil. Each radiator coil is preferably driven by driver circuitry to generate a field at a known frequency, distinct from that of other radiator coils, so that the signals generated by the sensor coil may be separated by frequency into components corresponding to the different radiator coils.

PCT Patent Publication WO 96/05768, U.S. Pat. No. 6,690,963 and the corresponding U.S. patent application Ser. No. 09/414,875, to Ben-Haim et al. (published as U.S. Patent Application Publication U.S. 2002/0065455 A1), whose disclosures are incorporated herein by reference, describe a system that generates six-dimensional position and orientation information regarding the tip of a catheter. This system uses a plurality of sensor coils adjacent to a locatable site in the catheter, for example near its distal end, and a plurality of radiator coils fixed in an external reference frame. These coils generate signals in response to magnetic fields generated by the radiator coils, which signals allow for the computation of six location and orientation coordinates.

U.S. Pat. No. 6,239,724 to Doron et al., whose disclosure is incorporated herein by reference, describes a telemetry system for providing spatial positioning information from within a patient's body. The system includes an implantable telemetry unit having (a) a first transducer, for converting a power signal received from outside the body into electrical power for powering the telemetry unit; (b) a second transducer, for receiving a positioning field signal that is received from outside the body; and (c) a third transducer, for transmitting a locating signal to a site outside the body, in response to the positioning field signal.

The above-mentioned U.S. patent application Ser. No. 10/029,473 to Govari, published as U.S. Patent Application Publication 2003/0120150, describes apparatus for tracking an object. The apparatus includes a plurality of field generators, which generate electromagnetic fields at different, respective frequencies in a vicinity of the object, and a radio frequency (RF) driver, which radiates a RF driving field toward the object. A wireless transponder is fixed to the object. The transponder includes at least one sensor coil, in which a signal current flows responsive to the electromagnetic fields, and a power coil, which receives the RF driving field and conveys electrical energy from the driving field to power the transponder. The power coil also transmits an output signal responsive to the signal current to a signal receiver, which processes the signal to determine coordinates of the object.

SUMMARY OF THE INVENTION

Embodiments of the present invention provide magnetic tracking systems for use in tracking the positions of objects within the body of a patient. In some embodiments, these systems are used in orthopedic procedures, such as implantation of implants such as screws, nails, rods or prosthetic joints or any other orthopedic device or tool. For this purpose, wireless magnetic position sensors may be inserted into the patient's bone, into implants such as screws, nails, rods or other orthopedic devices that can be inserted into the patient's bone or into prosthetic implants and into tools used during surgery. The track system determines the coordinates of the sensors, and thus enables the surgeon to visualize the locations and orientations of these elements while reducing or eliminating the need for intraoperative X-ray imaging. Implanted position sensors may also be used in post-operative follow-up.

The wireless magnetic position sensors generate position signals in response to magnetic fields that are produced by multiple field generators that are deployed outside the body. The intersection region of the magnetic fields that are produced by the various field generators defines a working volume, in which the tracking system is capable of determining the coordinates of the position sensors with accuracy sufficient for the medical procedure in question. The field generators are typically mounted on a reference structure that holds the field generators in fixed relative positions, but which is capable of moving relative to the patient. In this manner, the working volume of the tracking system can be conveniently positioned to cover the area of a surgical procedure, without interfering with the surgeon's ability to work in the area.

There is therefore provided, in accordance with an embodiment of the present invention, a surgical tracking system, including:

a wireless position sensor, which is adapted to be implanted in a bone of a subject, and responsively to externally-applied magnetic fields within a working volume of the tracking system, to generate and transmit sensor signals indicative of coordinates of the position sensor within the bone;

a plurality of field generator coils, which are adapted to generate the magnetic fields so as to define the working volume;

a reference structure, to which the field generator coils are fixed in predetermined locations, and which is movable relative to the subject in order to position the working volume so as to intercept the bone; and a system controller, which is coupled to receive and process the sensor signals so as to determine the coordinates of the position sensor within the bone.

In some embodiments, the reference structure includes multiple arms, each holding a respective one of the field generator coils, and a base, which is coupled to support the arms. The base is typically adapted to adjust at least one of a height, a rotation and a tilt of the arms, while maintaining the arms in a fixed mutual relation.

In other embodiments, the reference structure includes multiple arms, each holding a respective one of the field generator coils, and a boom, which is coupled to support the arms above the subject. Typically, the boom is adapted to adjust at least one of a height, a rotation and a tilt of the arms, while maintaining the arms in a fixed mutual relation. In one embodiment, the system includes a lamp, which is held over the subject by the boom so as to illuminate an area of the working volume.

Typically, the bone has an axis, and the locations at which the field generators are fixed to the reference structure define a plane, and the reference structure is adapted to position the field generators so that the plane is approximately parallel to the axis. Alternatively or additionally, the reference structure is adapted to position the field generators so that the plane is approximately perpendicular to the axis. In one such embodiment, the reference structure includes a semicircular holder, to which the field generators are fixed, and which partly surrounds the axis. The reference structure may also include a base, to which the semicircular holder is movably attached, so as to permit at least one of a height, a rotation and a tilt of the semicircular holder to be adjusted, while maintaining the field generators in a fixed mutual relation.

In another embodiment, the system includes an operating table having an underside and including a base, which contains the system controller, wherein the reference structure includes multiple arms, each holding a respective one of the field generator coils, and an articulated mount to which the arms are fixed and which is fixed to the underside of the table in order to support the arms. Typically, the articulated mount is adapted to adjust at least one of a height, a rotation and a tilt of the arms, while maintaining the arms in a fixed mutual relation.

In yet another embodiment, the reference structure is configured to be inserted into an opening in an operating table.

In disclosed embodiments, the position sensor includes one or more sensor coils, which are adapted to sense the magnetic fields so as to generate the sensor signals. In some embodiments, the system includes a driving antenna, which is adapted to radiate a radio frequency (RF) electromagnetic field toward the sensor, and the position sensor includes a power coil, which is coupled to receive the RF electromagnetic field so as to provide electrical power to the sensor. Additionally or alternatively, the position sensor includes a communication coil, which is coupled to transmit the sensor signals to the system controller.

In some embodiments, the system includes an implant that is a screw, which contains at least the one or more sensor coils of the position sensor, and which is adapted to be inserted into the bone. In some of these embodiments, the position sensor includes a power source, which is contained in the screw. In other embodiments, the position sensor includes an external unit, which includes at least a power source and is adapted to be positioned outside a body of the subject, and wires coupling the one or more sensor coils in the screw to the external unit.

In a disclosed embodiment, the system includes a surgical tool, for operating on the bone, the tool including a tool position sensor, which is adapted to generate and transmit, responsively to the externally-applied magnetic fields, tool signals indicative of coordinates of the tool relative to the bone.

There is also provided, in accordance with an embodiment of the present invention, a method for surgery, including:

implanting in a bone of a subject a wireless position sensor, which is adapted to generate and transmit sensor signals indicative of coordinates of the position sensor within the bone in response to externally-applied magnetic fields;

mounting a plurality of field generator coils in predetermined locations on a reference structure;

driving the field generator coils to generate the magnetic fields, thus defining a working volume for tracking the wireless position sensor;

moving the reference structure in order to position the working volume so as to intercept the bone; and receiving and processing the sensor signals so as to determine the coordinates of the position sensor within the bone.

The method may include performing a surgical procedure on the bone using a surgical tool including a tool position sensor, which is adapted to generate and transmit, responsively to the externally-applied magnetic fields, tool signals indicative of coordinates of the tool relative to the bone.

The present invention will be more fully understood from the following detailed description of the embodiments thereof, taken together with the drawings in which:

BRIEF DESCRIPTION OF THE DRAWINGS

FIGS. 3A and 3B are schematic, pictorial illustrations showing details of wireless position sensors, in accordance with embodiments of the present invention;

FIG. 4 is a schematic, pictorial illustration showing details of a two-part position sensor, in accordance with an embodiment of the present invention;

FIGS. 10A and 10B are schematic, pictorial illustrations of a magnetic tracking system for use in surgery, in accordance with still another embodiment of the present invention.

DETAILED DESCRIPTION OF EMBODIMENTS

Figure 1:
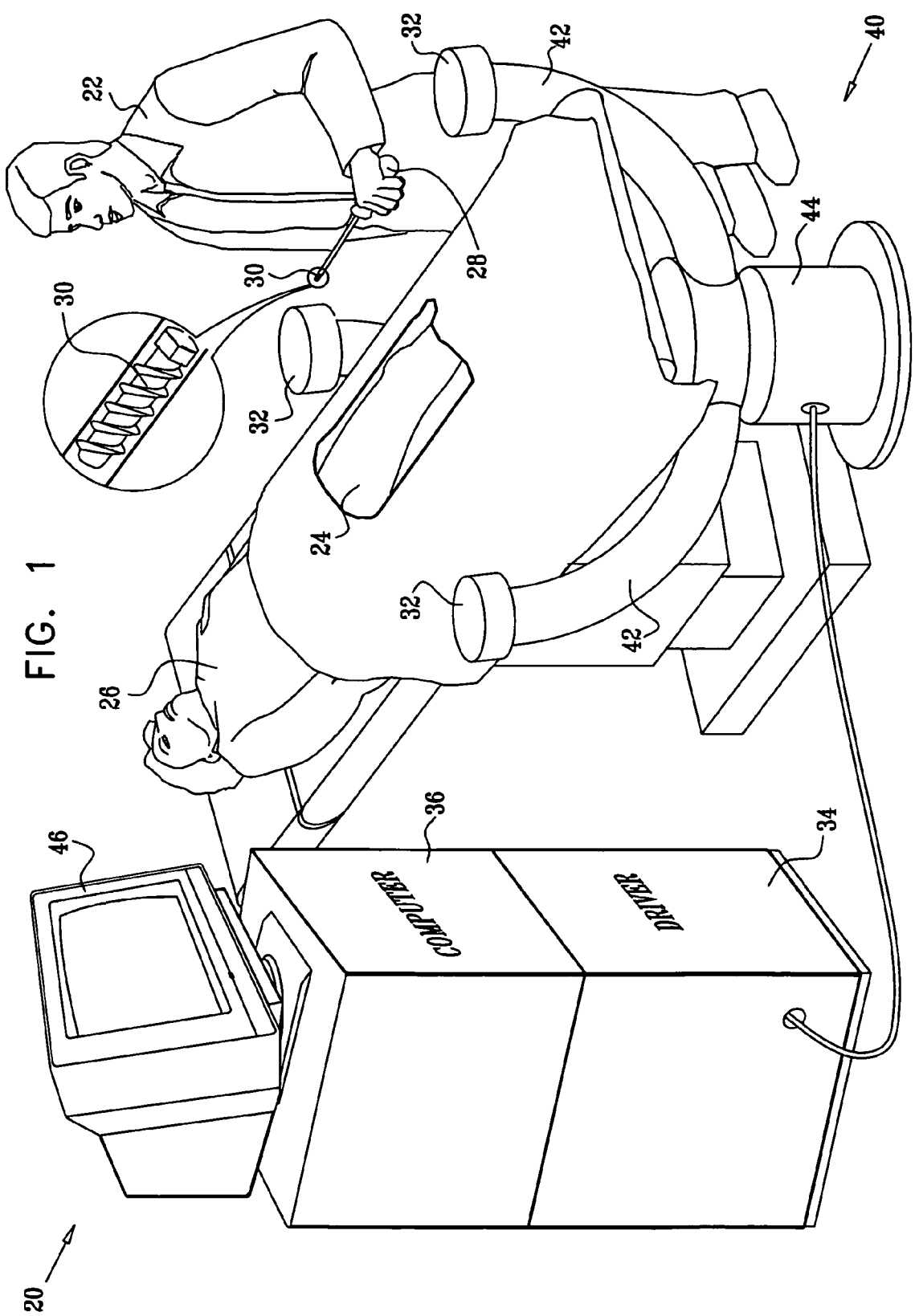
FIG. 1 is a schematic, pictorial illustration of a magnetic tracking system used in surgery, in accordance with an embodiment of the present invention.

FIG. 1 is a schematic, pictorial illustration of a magnetic tracking system 20 for use in surgery, in accordance with an embodiment of the present invention. In the pictured embodiment, a surgeon 22 is preparing to perform a procedure on a leg 24 of a patient 26. The surgeon uses a tool 28 to implant or place an implant, generally designated 30, (in this example a bone screw 30) in the bone of leg 24. Both the tool and the implant, i.e. the screw, contain miniature, wireless position sensors, which are described in detail hereinbelow. Each sensor generates and transmits signals that are indicative of its location and orientation coordinates, in response to an external magnetic field produced by a set of field generator coils 32 (also referred to as radiator coils). Typically, multiple screws 30 with position sensors are implanted by surgeon 22 at key locations in the patient's bone. Additionally or alternatively, similar position sensors may be fixed to other implants 30, such as a prosthetic joint or intramedullary insert or other implants 30 such as a nail, rod, pin, staple, bone or tissue anchor, or other orthopedic device, in order to permit the position of the implant 30 to be monitored, as well. For example, the use of such position sensors in a hip implant is shown in the above-mentioned U.S. patent application Ser. No. 10/029,473.

Field generator coils 32 are driven by driver circuits 34 to generate electromagnetic fields at different, respective sets of frequencies $\{\omega_1\}$, $\{\omega_2\}$ and $\{\omega_3\}$. Typically, the sets comprise frequencies in the approximate range of 100 Hz-30 kHz, although higher and lower frequencies may also be used. The sets of frequencies at which the coils radiate are set by a computer 36, which serves as the system controller for system 20. The respective sets of frequencies may all include the same frequencies, or they may include different frequencies. In any case, computer 36 controls circuits 34 according to a known multiplexing pattern, which provides that at any point in time, no more than one field generator coil is radiating at any given frequency. Typically, each driver circuit is controlled to scan cyclically over time through the frequencies in its respective set. Alternatively, each driver circuit may drive the respective coil 32 to radiate at multiple frequencies simultaneously.

For the purposes of system 20, coils 32 may be arranged in any convenient position and orientation, so long as they are fixed in respect to some reference frame, and so long as they are non-overlapping, that is, there are no two field generator coils with the exact, identical location and orientation. Typically, for surgical applications such as that shown in the figures, coils 32 comprise wound annular coils about 15-20 cm in outer diameter (O.D.) and about 1-2 cm thick, in a triangular arrangement, wherein the centers of the coils are about 80-100 cm apart. The coil axes may be parallel, as shown in this figure, or they may alternatively be inclined, as shown, for example, in FIGS. 6A and 6B. Bar-shaped transmitters or even triangular or square-shaped coils could also be useful for such applications.

In orthopedic and other surgical applications, it is desirable that coils 32 be positioned away from the surgical field, so as not to interfere with the surgeon's freedom of movement. On the other hand, the coils should be positioned so that the working volume of the tracking system includes the entire area in which the surgeon is operating. At the same time, the locations and orientations of coils 32 should be known relative to a given reference frame in order to permit the coordinates of tool 28 and screw 30 to be determined in that reference frame.

In order to meet these potentially-conflicting requirements, coils 32 are mounted on a reference structure 40. In the embodiment of FIG. 1, structure 40 comprises multiple arms 42, which are fixed to an articulated base 44. Alternative reference structures and configurations are shown in the figures that follow. Arms 42 hold coils 32 in known relative positions. Base 44, however, is capable of tilting, turning and changing the elevations of arms 42, so as to enable surgeon 22 to position coils 32 in convenient locations. The movement of base 44 may be controlled by computer 36, so that the computer is also aware of the actual locations of coils 32.

Alternatively or additionally, an image registration procedure may be used to calibrate the positions of coils 32 relative to patient 26. An exemplary registration procedure, based on X-ray imaging, is described in U.S. Pat. No. 6,314,310, whose disclosure is incorporated herein by reference. Further alternatively or additionally, a reference sensor, fixed to patient 26 or to the operating table in a known location, may be used for calibration. The use of reference sensors for this purpose is described, for example, in the above-mentioned U.S. Pat. No. 5,391,199.

The position sensors in screw 30 and tool 28 typically comprise sensor coils, in which electrical currents are induced to flow in response to the magnetic fields produced by field generator coils 32. An exemplary arrangement of the sensor coils is shown in FIG. 3A below. The sensor coils may be wound on either air cores or cores of magnetic material. Typically, each position sensor comprises three sensor coils, having mutually orthogonal axes, one of which is conveniently aligned with the longitudinal axis of tool 28 or of screw 30. The three coils may be concentrically wound on a single core, or alternatively, the coils may be non-concentrically wound on separate cores, and spaced along the longitudinal axis of the tool or screw. The use of non-concentric coils is described, for example, in the above-mentioned PCT Patent Publication WO 96/05768 and in the corresponding U.S. patent application Ser. No. 09/414,875. Alternatively, the position sensors may each comprise only a single sensor coil or two sensor coils. Further alternatively, screw 30 and tool 28 may comprise magnetic position sensors based on sensing elements of other types known in the art, such as Hall effect sensors.

At any instant in time, the currents induced in the sensor coils comprise components at the specific frequencies in sets $\{\omega_1\}$, $\{\omega_2\}$ and $\{\omega_3\}$ generated by field generator coils 32. The respective amplitudes of these currents (or alternatively, of time-varying voltages that may be measured across the sensor coils) are dependent on the location and orientation of the position sensor relative to the locations and orientations of the field generator coils. In response to the induced currents or voltages, signal processing and transmitter circuits in each position sensor generate and transmit signals that are indicative of the location and orientation of the sensor. These signals are received by a receiving antenna (shown, for example, in FIG. 6A), which is coupled to computer 36. The computer processes the received signals, together with a representation of the signals used to drive field generator coils 32, in order to calculate location and orientation coordinates of screw 30 and tool 28. The coordinates are used by the computer in driving a display 46, which shows the relative locations and orientations of the tool, screw and other elements (such as prosthetic implants) to which position sensors have been fixed.

Although in FIG. 1, system 20 is shown as comprising three field generator coils 32, in other embodiments of the present invention, different numbers, types and configurations of field generators and sensors may used. A fixed frame of reference may be established, for example, using only two non-overlapping field generator coils to generate distinguishable magnetic fields. Two non-parallel sensor coils may be used to measure the magnetic field flux due to the field generator coils, in order to determine six location and orientation coordinates (X, Y, Z directions and pitch, yaw and roll orientations) of the sensor. Using three field generator coils and three sensor coils, however, tends to improve the accuracy and reliability of the position measurement.

Alternatively, if only a single sensor coil is used, computer 36 can still determine five position and orientation coordinates (X, Y, Z directions and pitch and yaw orientations). Specific features and functions of a single coil system (also referred to as a single axis system) are described in U.S. Pat. No. 6,484,118, whose disclosure is incorporated herein by reference.

When a metal or other magnetically-responsive article is brought into the vicinity of an object being tracked, such as screw 30 or tool 28, the magnetic fields in this vicinity are distorted. In the surgical environment shown in FIG. 1, for example, there can be a substantial amount of conductive and permeable material, including basic and ancillary equipment (operating tables, carts, movable lamps, etc.), as well as invasive surgery apparatus (scalpels, scissors, etc., including tool 28 itself). The magnetic fields produced by field generator coils 32 may generate eddy currents in such articles, and the eddy currents then cause a parasitic magnetic field to be radiated. Such parasitic fields and other types of distortion can lead to errors in determining the position of the object being tracked.

In order to alleviate this problem, the elements of tracking system 20 and other articles used in the vicinity of the tracking system are typically made of non-metallic materials when possible, or of metallic materials with low permeability and conductivity. For example, reference structure 40 may be constructed using plastic or non-magnetic composite materials, as may other articles in this vicinity, such as the operating table. In addition, computer 36 may be programmed to detect and compensate for the effects of metal objects in the vicinity of the surgical site. Exemplary methods for such detection and compensation are described in U.S. Pat. Nos. 6,147,480 and 6,373,240, as well as in U.S. patent application Ser. No. 10/448,289 filed May 29, 2003 and Ser. No. 10/632,217 filed Jul. 31, 2003, all of whose disclosures are incorporated herein by reference.

Figure 2A:
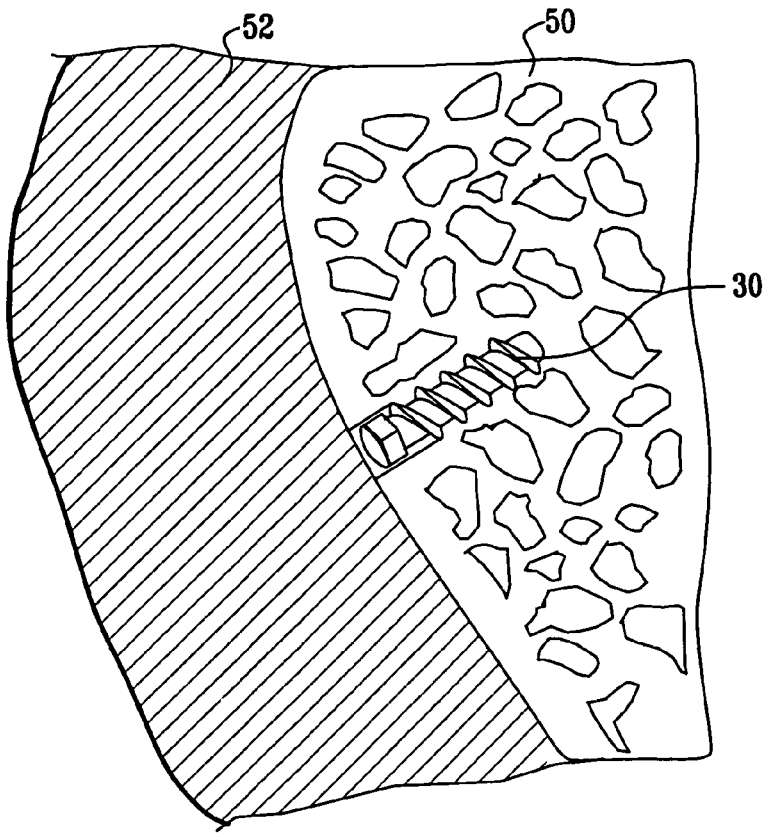
FIGS. 2A and 2B are schematic, partly sectional illustrations, showing insertion of implantable position sensors into the bone of a patient, in accordance with an embodiment of the present invention.

FIG. 2A is a schematic, sectional illustration showing implantation of screw 30 into a bone 50, such as the femur of patient 26, in accordance with an embodiment of the present invention. To insert the screw, surgeon 22 makes an incision through overlying soft tissue 52, and then rotates the screw into bone 50 using tool 28, for example. Alternatively, the screw may be inserted percutaneously, without prior incision. Note that in the embodiment of FIG. 2A, screw 30 has no wired connection to elements outside the body. Typically, screw 30 is between about 5 and 15 mm long, and is about 2-4 mm in diameter. To avoid interfering with reception and transmission of signals by the sensor that it contains, screw 30 typically comprises a non-magnetic material, which may comprise metals, alloys, ceramics, plastics or a combination of such materials. The configuration and operation of the circuits in screw 30 are described hereinbelow with reference to FIGS. 3A and 3B.

Figure 2B:
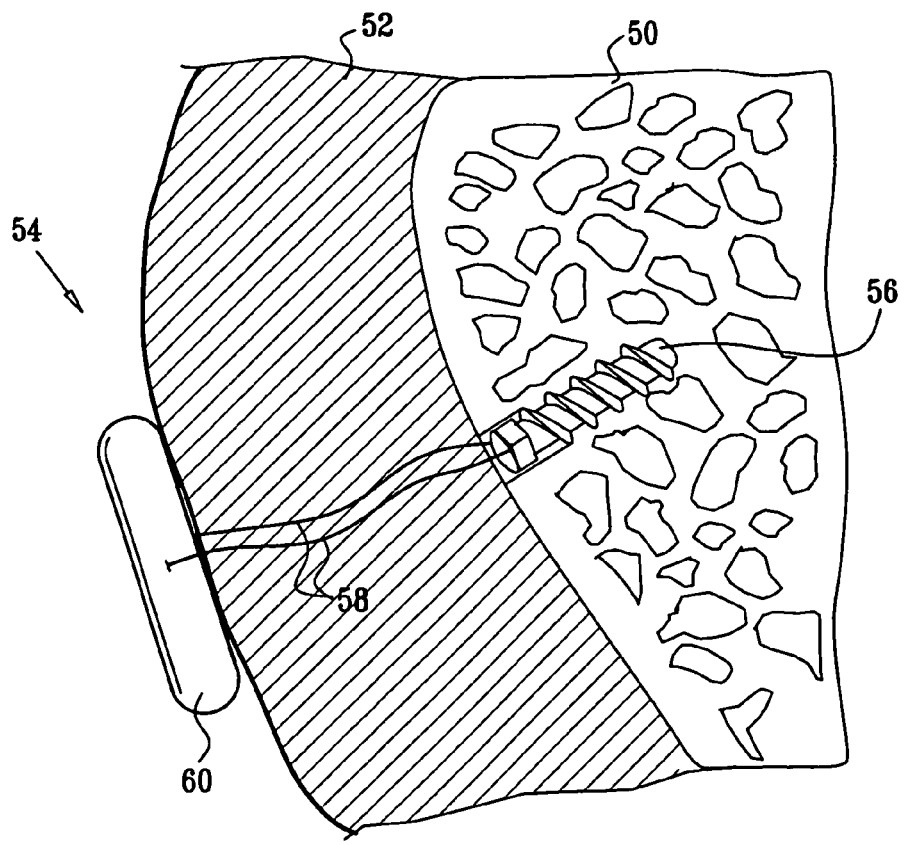

FIG. 2B is a schematic, sectional illustration showing another position sensor device 54, in accordance with an alternative embodiment of the present invention. Device 54 comprises an implantable screw 56, which is coupled by wires 58 to an external unit 60. Screw 56 is inserted into bone 50 in substantially the same manner as is screw 30 (leaving wires 58 to pass out of the patient's body through soft tissue 52). In this case, however, because some elements of device 54 are contained in external unit 60, screw 56 may generally be made smaller than screw 30. For example, screw 56 may be between about 5 and 10 mm long, and between about 2 and 4 mm in diameter. The reduced screw size is helpful in reducing trauma and possible damage to bone 50. Further details of device 54 are shown in FIG. 4.

FIG. 3A is a schematic, pictorial illustration of a wireless position sensor 70 that is contained in screw 30, in accordance with an embodiment of the present invention. Sensor 70 in this embodiment comprises three sets of coils: sensor coils 72, power coils 74, and a communication coil 76. Alternatively, the functions of the power and communication coils may be combined, as described in the above-mentioned U.S. patent application Ser. No. 10/029,473. Further alternatively, although communication coil 76 is shown in FIG. 3A to be wound in a plane that is perpendicular to the longitudinal axis of screw 30, the communication coil or antenna may alternatively be arranged along the length of sensor 70, roughly parallel to the longitudinal axis of the screw. Coils 72, 74 and 76 are coupled to electronic processing circuitry 78, which is mounted on a suitable substrate 80, such as a flexible printed circuit board (PCB). Details of the construction and operation of circuitry 78 are described in U.S. patent application Ser. No. 10/029,473 and in the above-mentioned U.S. patent application Ser. No. 10/706,298 which are incorporated herein by reference.

Although for simplicity, FIG. 3A shows only a single sensor coil 72 and a single power coil 74, in practice sensor 70 typically comprises multiple coils of each type, such as three sensor coils and three power coils. The sensor coils are wound together, in mutually-orthogonal directions, on a sensor core 82, while the power coils are wound together, in mutually-orthogonal directions, on a power core 84. Typically, each of the three power coils comprises about 30-40 turns of wire having a diameter of at least about 40 μm, while power core 84 is a ferrite cube of about 1.5-2 mm on a side. Each of the three sensor coils typically comprises between about 700 and 3000 turns of 11 μm diameter wire, while sensor core 82 is a ferrite cube of about 1.8-2.4 on a side. (It will be understood that these dimensions are given by way of example, and the dimensions may in practice vary over a considerable range.) Alternatively, the sensor and power coils may be overlapped on the same core, as described, for example in U.S. patent application Ser. No. 10/754,751, filed Jan. 9, 2004, whose disclosure is incorporated herein by reference. It is generally desirable to separate the coils one from another by means of a dielectric layer (or by interleaving the power and sensor coils when a common core is used for both) in order to reduce parasitic capacitance between the coils.

In operation, power coils 74 serve as a power source for sensor 70. The power coils receive energy by inductive coupling from an external driving antenna (shown, for example, in FIG. 6A). Typically, the driving antenna radiates an intense electromagnetic field at a relatively high radio frequency (RF), such as in the range of 13.5 MHz. The driving field causes currents to flow in coils 74, which are rectified in order to power circuitry 78. Meanwhile, field generator coils 32 (FIG. 1) induce time-varying signal voltages to develop across sensor coils 72, as described above. Circuitry 78 senses the signal voltages, and generates output signals in response thereto. The output signals may be either analog or digital in form. Circuitry 78 drives communication coil 76 to transmit the output signals to a receiving antenna (also shown in FIG. 6A) outside the patient's body. Typically, the output signals are transmitted at still higher radio frequencies, such as frequencies in the rage of 43 MHz or 915 MHz, using a frequency-modulation scheme, for example. Additionally or alternatively, coil 76 may be used to receive control signals, such as a clock signal, from a transmitting antenna (not shown) outside the patient's body. Although certain frequency ranges are cited above by way of example, those skilled in the art will appreciate that other frequency ranges may be used for the same purposes.

In another embodiment, not shown in the figures, sensor coils 72 are non-concentric. In this embodiment, each of the sensor coils typically has an inner diameter of about 0.5-1.3 mm and comprises about 2000-3000 turns of 11 μm diameter wire, giving an overall coil diameter of about 1-1.9 mm. (As above, these dimensions are given only by way of example, and the actual dimensions may vary.) The wire size of the sensor coils can range from 10-31 μm, and the number of turns between 300 and more than 3000, depending on the maximum allowable size and the wire diameter. The effective capture area of the sensor coils is typically made as large as feasible, consistent with the overall size requirements. The sensor coils are typically cylindrical, but other shapes can also be used. For example, barrel-shaped or square coils may be useful, depending on the geometry of screw 30.

FIG. 3B is a schematic, pictorial illustration of a wireless position sensor 90, in accordance with another embodiment of the present invention. Sensor 90 differs from sensor 70, in that sensor 90 comprises a battery 92 as its power source, instead of power coils 74. Battery 92 may be of any suitable type, either single-use or rechargeable. In other respects, the operation of sensor 90 is substantially similar to that of sensor 70, as described above. Use of battery 92 has the advantages of supplying higher operating power to electronic processing circuitry 78, while avoiding the need to irradiate patient 26 with an intense electromagnetic field in order to provide inductive RF power to the sensor. On the other hand, incorporating battery 92 in sensor 90 typically increases the length of the sensor, by comparison to sensor 70, and therefore may require the use of a longer screw 30 to contain the sensor. In addition, the operating lifetime of sensor 70 is effectively unlimited, while that of sensor 90 is limited by the lifetime of battery 92.

FIG. 4 is a schematic, pictorial illustration showing details of device 54, in accordance with an embodiment of the present invention. The external features of device 54 and its implantation in bone 50 were described above with reference to FIG. 2B. Device 54 comprises an internal sensing unit 94, which is contained in screw 56. Typically, sensing unit 94 contains only sensor coils 72, and possibly or optionally elements of circuitry 78. This arrangement allows the size of screw 56 to be minimized. External unit 60 typically contains a battery 96 and circuit elements 98, which comprise some or all of circuitry 78 (depending on how much of circuitry 78 is located within sensing unit 94), as well as communication coil 76. The battery may thus be replaced when necessary, without removing screw 56 from the bone. On the other hand, whereas sensors 70 and 90 are contained completely within screw 30, and thus leave no elements protruding outside the patient's body, device 54 can operate only when external unit 60 is connected outside the body to wires 58 that are operatively connected to sensing unit 94 and communicate with sensing unit 94.

Figure 5:
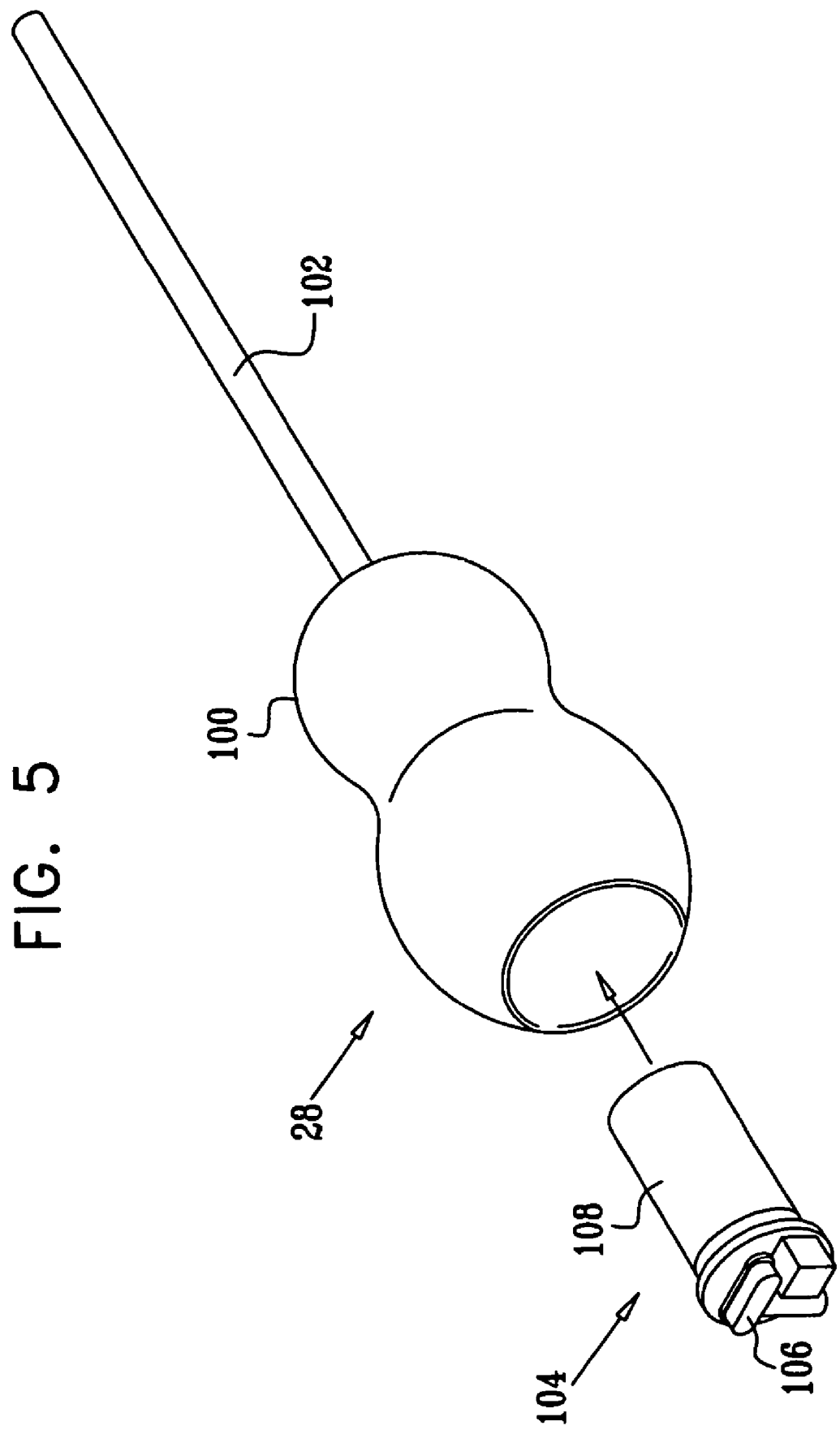
FIG. 5 is a schematic, pictorial illustration showing a surgical tool and a position sensor used to track coordinates of the tool, in accordance with an embodiment of the present invention.

FIG. 5 is a schematic, pictorial illustration showing details of tool 28, in accordance with an embodiment of the present invention. Tool 2-8 comprises a handle 100 and a shaft 102. A tool sensor 104 fits snugly into a suitable receptacle inside handle 100. Sensor 104 comprises sensing and communication circuits 106, which are powered by a battery 108. Typically, circuits 106 comprise three sensing coils, a communication coil and processing circuitry, as in sensor 90 (FIG. 3B). The sensing coils are similar to coils 72, and sense the location and orientation of sensor 104 relative to the magnetic fields generated by field generator coils 32 (FIG. 1). The communication coil conveys position signals to computer 36. The operation of circuits 106 is thus similar to that of the circuits in sensors 70 and 90, although elements of circuits 106 may be made larger and consume greater power than the corresponding elements in sensors 70 and 90.

Tool sensor 104 may be permanently housed inside tool 28, or the sensor may alternatively be removable (to replace battery 108, for example). Because the geometry of tool 28 is known, the location and orientation of handle 100, as indicated by sensor 104, indicates precisely the location and orientation of the distal tip of shaft 102. Alternatively, the tool sensor 104 may be miniaturized and may thus be contained inside shaft 102. Optionally, the tool sensor 104 may be calibrated before use in order to enhance the precision with which the shaft position is measured.

Figure 6A:
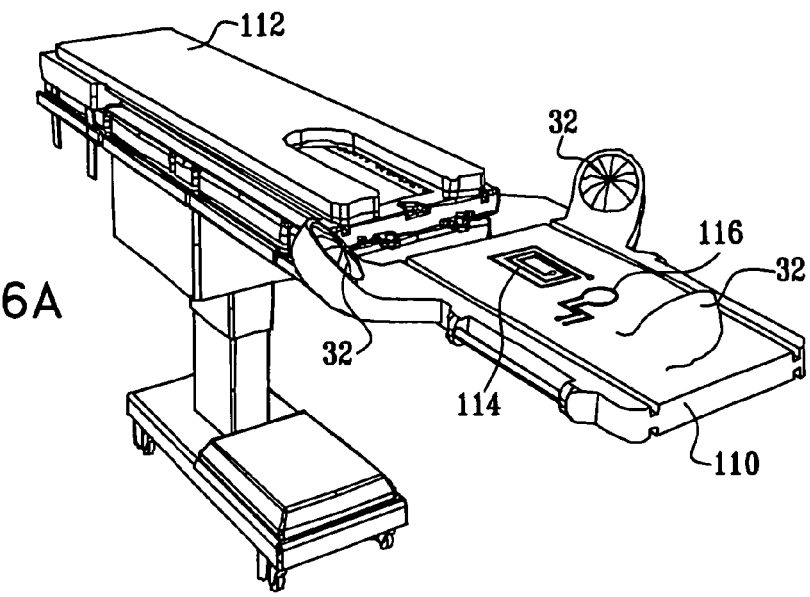
FIG. 6A is a schematic, pictorial illustration showing an operating table and a location pad that is inserted into the table, in accordance with an embodiment of the present invention.
Figure 6B:
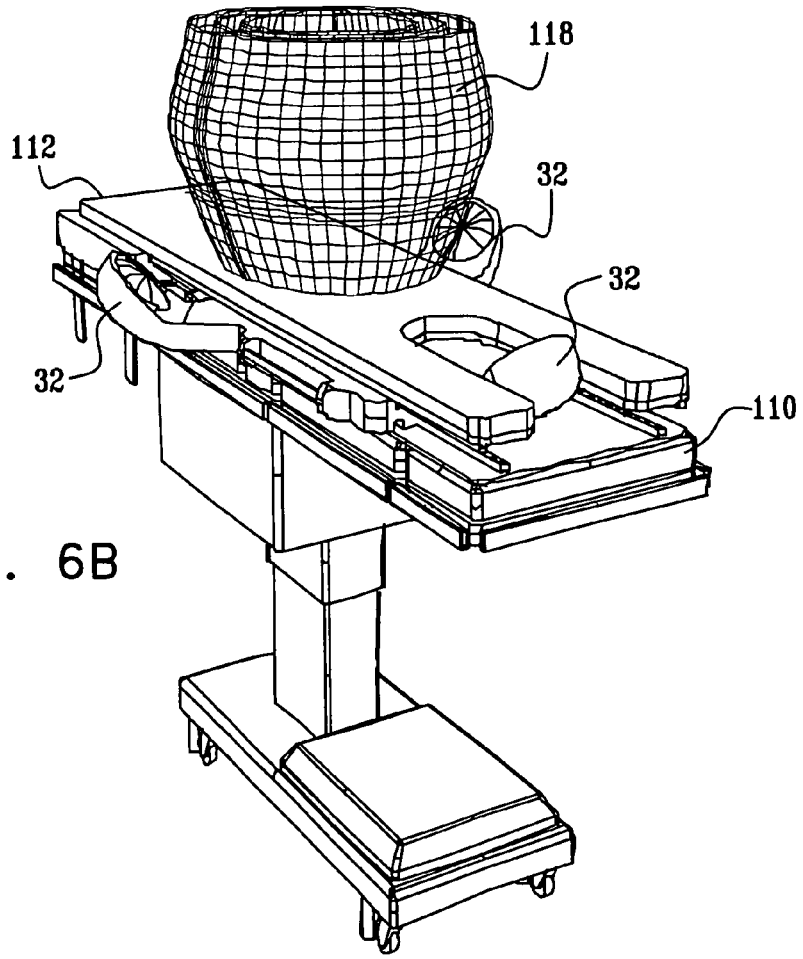
FIG. 6B is a schematic, pictorial illustration showing the location pad of FIG. 6A after insertion into the operating table, and showing the working volume of the location pad, in accordance with an embodiment of the present invention.

FIGS. 6A and 6B are schematic, pictorial illustrations showing insertion of a location pad 110 into an opening in an operating table 112, in accordance with an embodiment of the present invention. Pad 110 may be used as the reference structure in system 20 (FIG. 1), in place of structure 40. Pad 110 comprises an integral unit, which holds three field generator coils 32 in fixed positions. The unit is typically made from non-magnetic material, such as carbon fiber, fiberglass, plastic or ceramic. The field generator coils in this case are angled diagonally inward. In FIG. 6A pad 110 is shown prior to insertion into the table, while in FIG. 6B the pad has been slid into place.

Location pad 110 is also seen in FIG. 6A to comprise an optional power coil 114 and a communication coil 116. Power coil 114 is coupled by wires (not shown) to driver circuits 34, and generates an electromagnetic field to provide power inductively to power coils 74 in sensor 70 (FIG. 3A), as described above. (When a battery-powered sensor is used, the power coil is not required.) Communication coil 116 receives signals transmitted by communication coil 76 in sensors that are implanted in the patient's body, as well as from tool sensor 104. Communication coil 116 may also be used to transmit control signals, such as a clock signal, to the implanted sensors and tool sensor. Communication coil 116 is coupled by wires (not shown) to computer 36. The computer processes the signals received from communication coil 116 in order to determine the locations and orientations of the sensors. Coils 114 and 116 may be printed on the surface of pad 110, as shown in FIG. 6A, or they may alternatively comprise printed circuit traces or wire-wound coils contained inside pad 110.

FIG. 6B schematically shows a working volume 118 created by field generator coils 32 when driven by driver circuits 34. The surface of the working volume represents the outer limit of the region in which tracking system 20 is able to determine sensor coordinates to within a certain accuracy i.e. the location coordinates or position and orientation coordinates of the sensor. The required accuracy is determined by functional considerations, such as the degree of positioning precision required by surgeon 22 in performing the surgical procedure at hand. Typically, the outer surface of working volume 118 represents the limit in space at which tracking accuracy drops to the range of 1-2 mm. Tilting the field generator coils, as shown in FIGS. 6A and 6B, typically lowers the centroid of the working volume. Because pad 110 is rigid, it cannot be raised and lowered or tilted, as can structure 40 in FIG. 1. Pad 110 may, however, be slid in and out of table 112 in order to shift the position of working volume 118 along the table, so that the working volume intercepts the bone 50 or portion of the bone 50 on which the surgeon in to operate.

Figure 7:
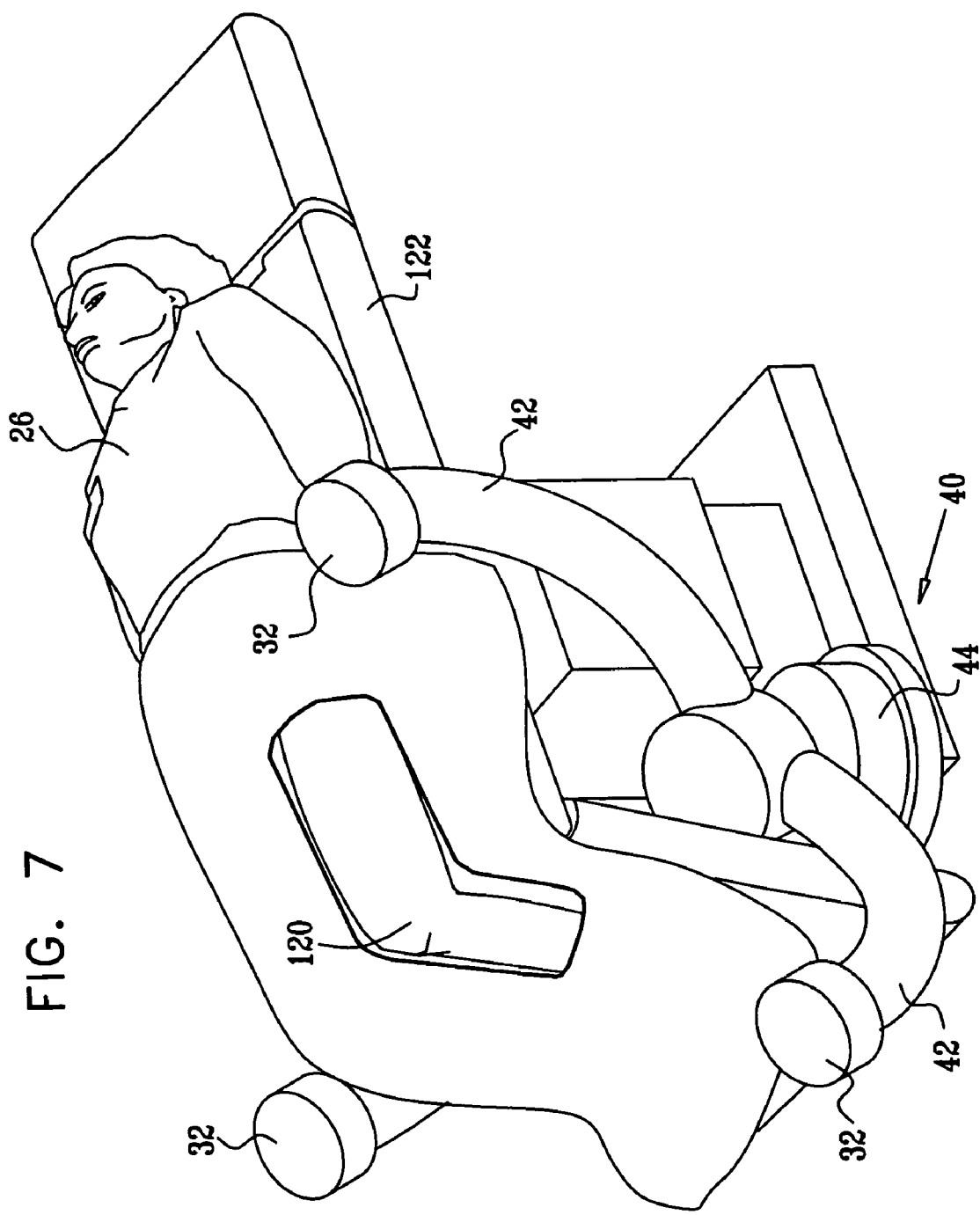
FIG. 7 is a schematic, pictorial illustration showing adjustment of the magnetic tracking system of FIG. 1 for use in a knee operation, in accordance with an embodiment of the present invention.

FIG. 7 is a schematic, pictorial illustration showing how reference structure 40 may be adjusted for use in surgery on a knee 120 of patient 26, in accordance with an embodiment of the present invention. The patient lies on an operating table 122, which folds as shown in the picture to give the surgeon convenient access to the patient's knee joint. Base 44 of structure 40 tilts accordingly, so that the working volume of field generator coils 32 encompasses the area of knee 120, while still permitting the surgeon unimpeded access to the area.

Figure 8:
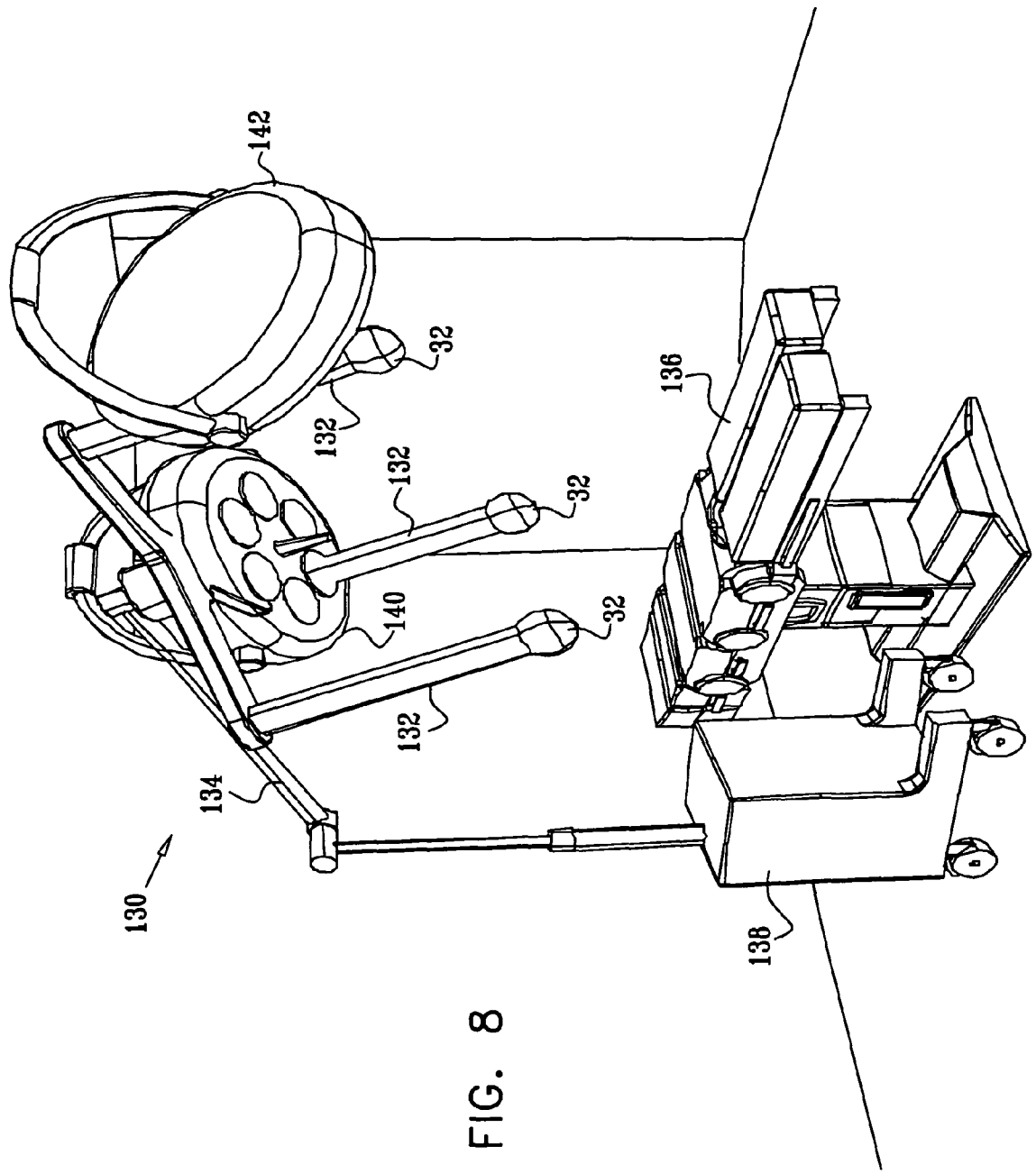
FIG. 8 is a schematic, pictorial illustration of a magnetic tracking system for use in surgery, in accordance with another embodiment of the present invention.

FIG. 8 is a schematic, pictorial illustration showing a reference structure 130 for supporting field generator coils 32, in accordance with another embodiment of the present invention. Structure 130 comprises arms 132, which hold coils 32. The arms are fixed to an articulated boom 134, which permits the height and angle of the field generator coils 32 to be adjusted relative to the position of the patient on an operating table 136. Boom 134 may be carried by a wheeled cart 138, so that structure 130 can be positioned at either side of table 136 or at the foot or head of the table. Cart 138 may also contain computer 36 and/or driver circuits 34. To reduce clutter over operating table 136, structure 130 may be integrated with an overhead lamp 140, as shown in the figure. In this configuration, lamp 140 illuminates the area of the working volume of coils 32. An additional lamp 142 is shown for completeness.

Figure 9:
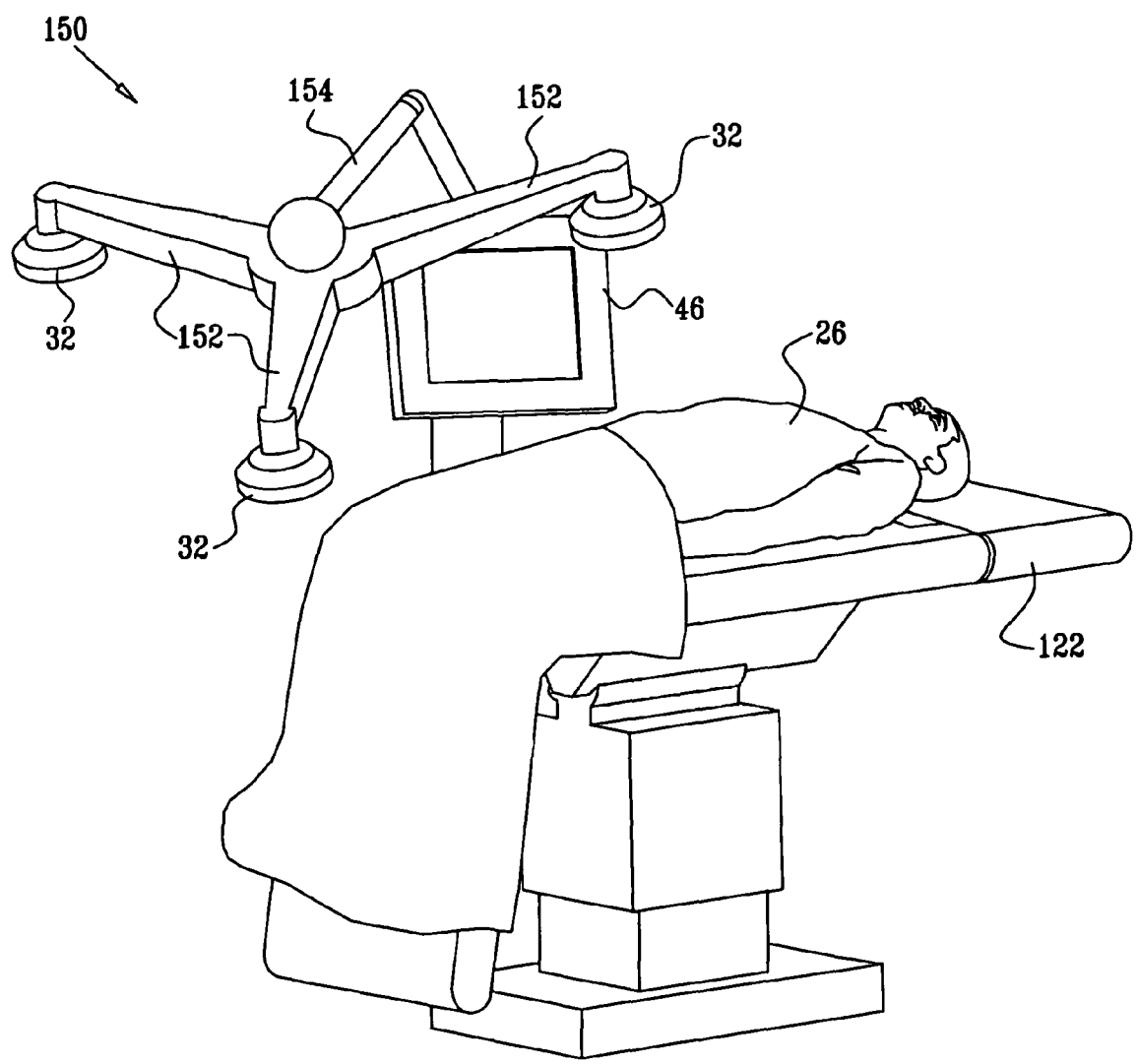
FIG. 9 is a schematic, pictorial illustration of a magnetic tracking system for use in surgery, in accordance with yet another embodiment of the present invention.

FIG. 9 is a schematic, pictorial illustration showing a reference structure 150 supporting field generator coils 32, in accordance with yet another embodiment of the present invention. Structure 150 comprises an articulated boom 154, which holds arms 152 to which coils 32 are attached. In this embodiment, structure 150 is tilted and positioned over the area of the patient's knees, to provide functionality similar to that shown in FIG. 7.

Figure 10A:
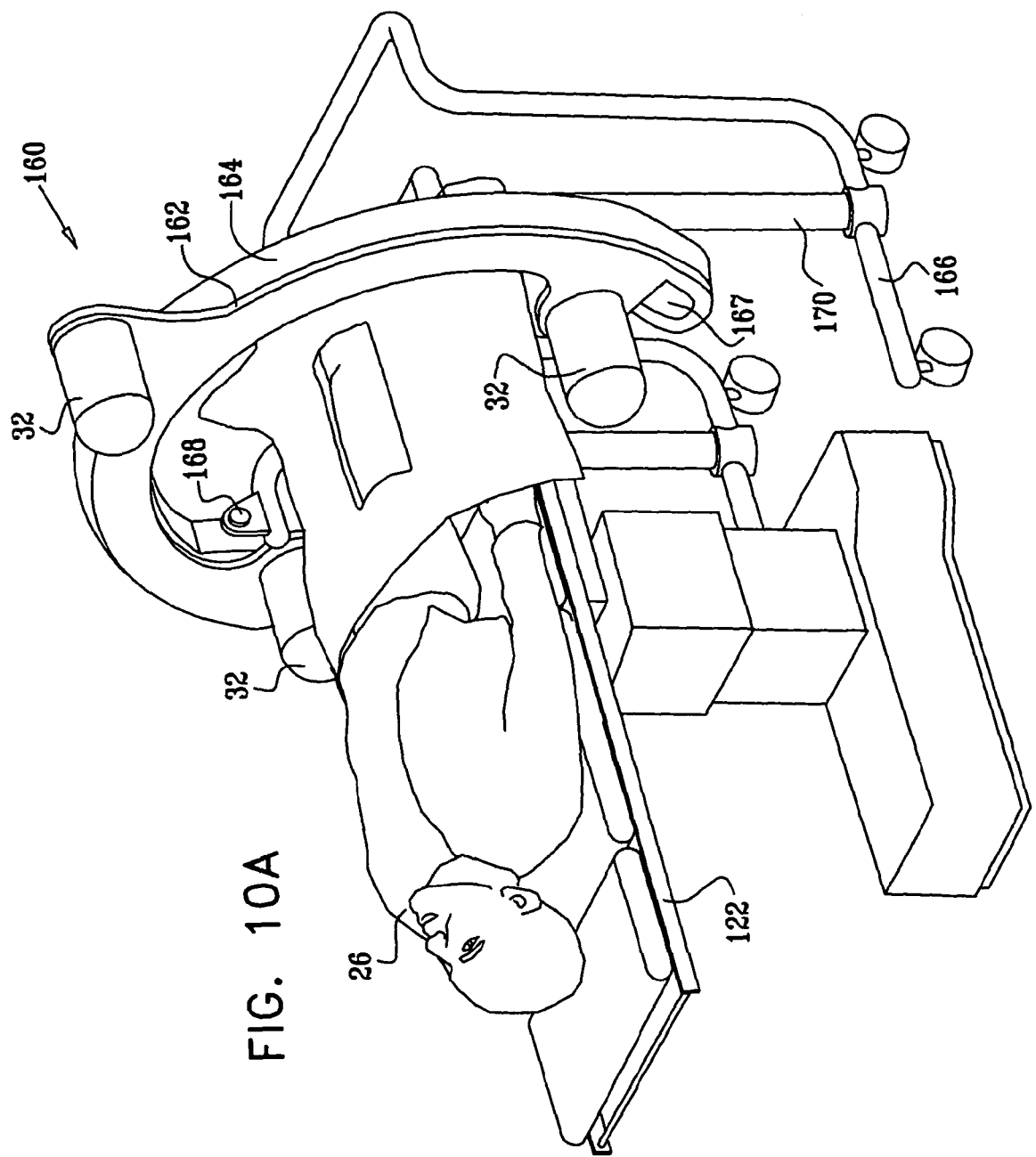

FIGS. 10A and 10B are schematic, pictorial illustrations showing another reference structure 160, in accordance with a further embodiment of the present invention. Structure 160 comprises a semicircular holder 162 for field generator coils 32, which is mounted on a base 164. Whereas the reference structures in the embodiments shown above are configured to position coils 32 in a plane that is roughly parallel to the long axis of the bone to be operated upon (such as the femur or the fibula), the plane of structure 160 is roughly perpendicular to this axis. Typically, for proper positioning of the working volume, structure 160 is placed so that the bone axis passes through the circle defined by the positions of coils 32, i.e., so that holder 162 partly surrounds the bone axis.

Structure 160 may be mounted on a cart 166 with wheels, enabling it to be positioned either at the foot (FIG. 10A) or head (FIG. 10B) of table 122. An adjustment slot 167 or other mechanism in base 164 permits holder 162 to rotate about the patient. A hinge permits base 164 to tilt, while telescopic legs 170 permit the entire structure to be raised or lowered. Structure 160 may thus be positioned flexibly, at the convenience of the surgeon, depending on the type of procedure that is to be carried out. The configuration of FIG. 10A, for example, may be convenient for hip surgery, while that of FIG. 10B is convenient for knee surgery.

Figure 11:
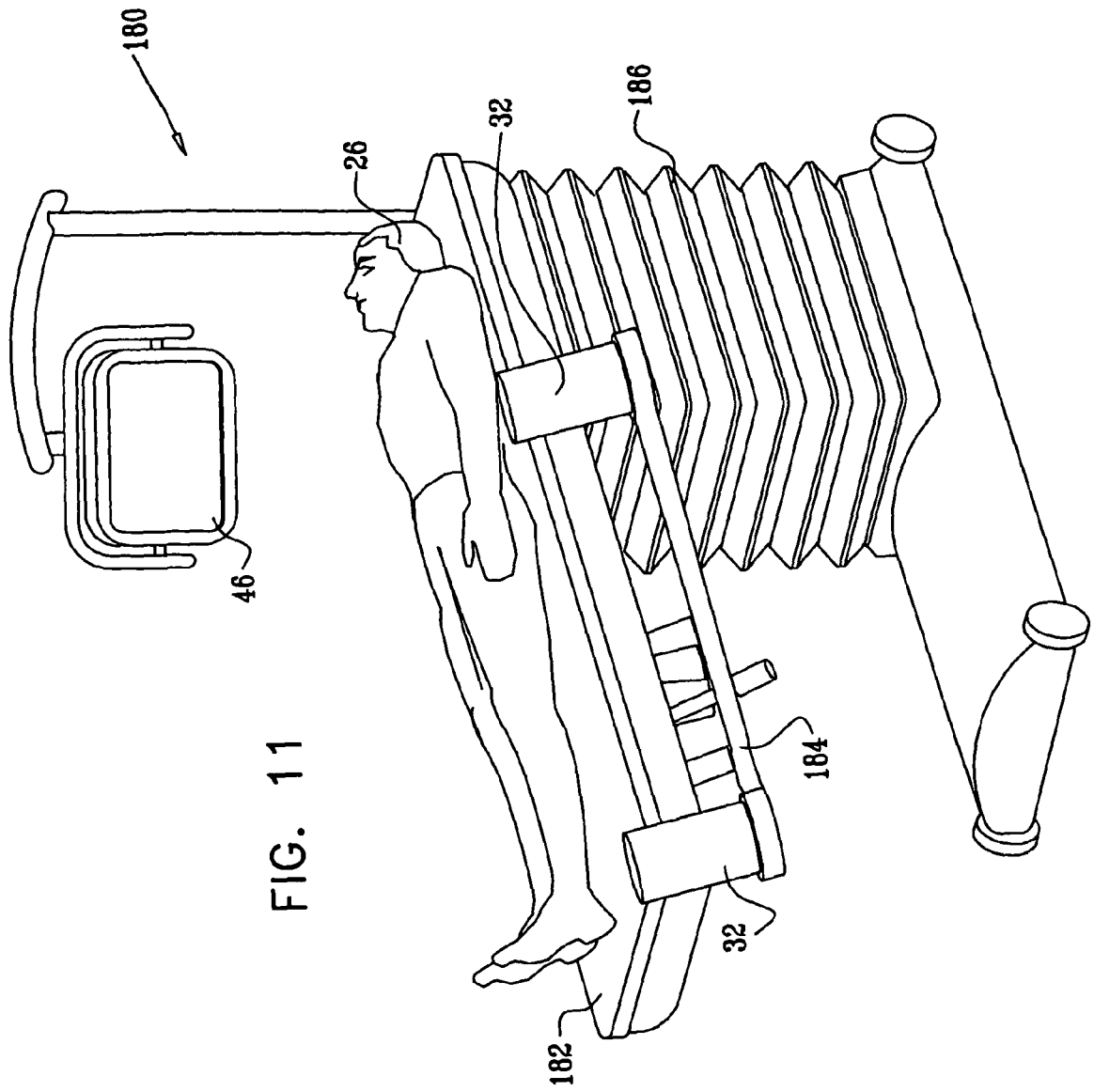
FIG. 11 is a schematic, pictorial illustration of a magnetic tracking system for use in surgery, in accordance with a further embodiment of the present invention.

FIG. 11 is a schematic, pictorial illustration showing a magnetic tracking system 180 for use in surgery, in accordance with still another embodiment of the present invention. In this embodiment, the tracking system is integrated into an operating table 182. The operating table may be custom-made for this purpose, and may thus comprise little or no magnetic material. A reference structure 184 is fixed to the underside of table 182 by an articulated mount that permits structure 184 to be rotated, tilted, raised and lowered, so as to position field generator coils 32 as required for the surgical procedure in question. A telescopic base 186 of table 182 contains driver circuits 34 and computer 36. Positions and orientations of position sensors and tools are shown on display 46, which is likewise integrated with table 182. System 180 thus permits the surgeon to operate with only minimal added encumbrance due to the use of magnetic position tracking.

Although the embodiments described hereinabove relate specifically to tracking systems that use time-varying magnetic fields, the principles of the present invention may also be applied, mutatis mutandis, in other sorts of tracking systems, such as ultrasonic tracking systems and tracking systems based on DC magnetic fields. It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A surgical tracking system for use by a surgeon, comprising:

a wireless position sensor, which is adapted to be implanted in a bone of a subject, and generates and transmits sensor signals responsive to externally-applied magnetic fields within a working volume of the tracking system, the sensor signals indicative of coordinates of the position sensor within the bone;

a plurality of field generator coils, which are adapted to generate the magnetic fields so as to define the working volume, the location and orientation of the plurality of field generator coils being known relative to a given reference frame;

a reference structure, to which the field generator coils are fixed in predetermined locations, and which is movable relative to the subject by the surgeon during surgery, the reference structure and the field generator coils being raised, lowered, tilted or shifted by the surgeon during surgery in order to shift the working volume so as to intercept the bone; and a system controller, which is coupled to receive and process the sensor signals so as to determine the coordinates of the position sensor within the bone and within the given reference frame.

2. The system according to claim 1, wherein the reference structure comprises:

multiple arms, each holding a respective one of the field generator coils; and a base, which is coupled to support the arms.

3. The system according to claim 2, wherein the base is adapted to adjust at least one of a height, a rotation and a tilt of the arms, while maintaining the arms in a fixed mutual relation.

4. The system according to claim 1, wherein the reference structure comprises:

multiple arms, each holding a respective one of the field generator coils; and a boom, which is coupled to support the arms above the subject.

5. The system according to claim 4, wherein the boom is adapted to adjust at least one of a height, a rotation and a tilt of the arms, while maintaining the arms in a fixed mutual relation.

6. The system according to claim 4, and comprising a lamp, which is held over the subject by the boom so as to illuminate an area of the working volume.

7. The system according to claim 1, wherein the bone has an axis, and wherein the locations at which the field generators are fixed to the reference structure define a plane, and
wherein the reference structure is adapted to position the field generators so that the plane is approximately parallel to the axis.

8. The system according to claim 1, wherein the bone has an axis, and wherein the locations at which the field generators are fixed to the reference structure define a plane, and
wherein the reference structure is adapted to position the field generators so that the plane is approximately perpendicular to the axis.

9. The system according to claim 8, wherein the reference structure comprises a semicircular holder, to which the field generators are fixed, and which partly surrounds the axis.

10. The system according to claim 9, wherein the reference structure comprises a base, to which the semicircular holder is movably attached, so as to permit at least one of a height, a rotation and a tilt of the semicircular holder to be adjusted, while maintaining the field generators in a fixed mutual relation.

11. The system according to claim 1, and comprising an operating table having an underside and comprising a base, which contains the system controller,
wherein the reference structure comprises multiple arms, each holding a respective one of the field generator coils, and an articulated mount to which the arms are fixed and which is fixed to the underside of the table in order to support the arms.

12. The system according to claim 11, wherein the articulated mount is adapted to adjust at least one of a height, a rotation and a tilt of the arms, while maintaining the arms in a fixed mutual relation.

13. The system according to claim 1, wherein the reference structure is configured to be inserted into an opening in an operating table.

14. The system according to claim 1, wherein the position sensor comprises one or more sensor coils, which are adapted to sense the magnetic fields so as to generate the sensor signals.

15. The system according to claim 14, and comprising a driving antenna, which is adapted to radiate a radio frequency (RF) electromagnetic field toward the sensor, and
wherein the position sensor comprises a power coil, which is coupled to receive the RF electromagnetic field so as to provide electrical power to the sensor.

16. The system according to claim 14, wherein the position sensor comprises a communication coil, which is coupled to transmit the sensor signals to the system controller.

17. The system according to claim 14, and comprising a screw, which contains at least the one or more sensor coils of the position sensor, and which is adapted to be inserted into the bone.

18. The system according to claim 17, wherein the position sensor comprises a power source, which is contained in the screw.

19. The system according to claim 17, wherein the position sensor comprises:
an external unit, which comprises at least a power source and is adapted to be positioned outside a body of the subject; and
wires coupling the one or more sensor coils in the screw to the external unit.

20. The system according to claim 1, and comprising a surgical tool, for operating on the bone, the tool comprising a tool position sensor, which is adapted to generate and transmit sensor signals responsive to the externally-applied magnetic fields, the sensor signals indicative of coordinates of the tool relative to the bone.

21. A method for surgery, comprising:
implanting in a bone of a subject a wireless position sensor, which is adapted to generate and transmit sensor signals responsive to externally-applied magnetic fields, the sensor signals indicative of coordinates of the position sensor within the bone;
mounting a plurality of field generator coils in predetermined locations on a reference structure, the location and orientation of the plurality of field generator coils being known relative to a given reference frame;
driving the field generator coils to generate the magnetic fields, thus defining a working volume for tracking the wireless position sensor;
moving the reference structure and the field generator coils by a surgeon during surgery by raising, lowering, tilting or shifting the reference structure and the field generator coils in order to shift the working volume so as to intercept the bone; and
receiving and processing the sensor signals so as to determine the coordinates of the position sensor within the bone and within the given reference frame.

22. The method according to claim 21, further comprising providing a reference structure comprising:
multiple arms, each holding a respective one of the field generator coils; and
a base, which is coupled to support the arms.

23. The method according to claim 22, wherein moving the reference structure comprises adjusting at least one of a height, a rotation and a tilt of the arms, while maintaining the arms in a fixed mutual relation.

24. The method according to claim 21, further comprising providing a reference structure comprising:
multiple arms, each holding a respective one of the field generator coils; and
a boom, which is coupled to support the arms above the subject.

25. The method according to claim 24, wherein moving the reference structure comprises adjusting at least one of a height, a rotation and a tilt of the arms, while maintaining the arms in a fixed mutual relation.

26. The method according to claim 21, further comprising fixing the field generators to the reference structure to define a plane, and positioning the field generators so that the plane is approximately parallel to an axis of the bone.

27. The method according to claim 21, further comprising fixing the field generators to the reference structure to define a plane, and positioning the field generators so that the plane is approximately perpendicular to an axis of the bone.

28. The method according to claim 27, further comprising providing a reference structure comprising a semicircular holder, to which the field generators are fixed, and which partly surrounds the axis.

29. The method according to claim 28, further comprising providing a reference structure comprising a base, to which the semicircular holder is movably attached, and moving the reference structure by adjusting at least one of a height, a rotation and a tilt of the semicircular holder relative to the base, while maintaining the field generators in a fixed mutual relation.

30. The method according to claim 21, further comprising providing a reference structure comprising multiple arms, each holding a respective one of the field generator coils, and an articulated mount to which the arms are fixed and which is fixed to the underside of an operating table in order to support the arms.

31. The method according to claim 30, further comprising moving the reference structure by adjusting at least one of a height, a rotation and a tilt of the arms, while maintaining the arms in a fixed mutual relation.

32. The method according to claim 21, further comprising providing a reference structure that is configured to be inserted into an opening in an operating table.

33. The method according to claim 21, further comprising providing a position sensor that comprises one or more sensor coils, which are adapted to sense the magnetic fields so as to generate the signals indicative of the coordinates.

34. The method according to claim 33, wherein the position sensor comprises a power coil, which is coupled to receive a radio frequency (RF) electromagnetic field so as to provide electrical power to the sensor, and wherein the method comprises radiating the RF electromagnetic field toward the sensor using a driving antenna.

35. The method according to claim 33, further comprising providing a position sensor that comprises a communication coil, which is coupled to transmit the sensor signals.

36. The method according to claim 33, wherein implanting the wireless position sensor comprises inserting at least the one or more sensor coils of the position sensor into a screw, and inserting the screw into the bone.

37. The method according to claim 36, further comprising providing a position sensor that comprises a power source, which is contained in the screw.

38. The method according to claim 36, wherein implanting the wireless position sensor comprises coupling the one or more sensor coils in the screw to an external unit outside a body of the subject, the external unit comprising at least a power source.

39. The method according to claim 21, and comprising performing a surgical procedure on the bone using a surgical tool comprising a tool position sensor, which is adapted to generate and transmit sensor signals, responsive to the externally-applied magnetic fields, the sensor signals indicative of coordinates of the tool relative to the bone.

* * * * *